United States Patent [19]

Keplinger et al.

[11] Patent Number: 5,723,625

[45] Date of Patent: Mar. 3, 1998

[54] PROCESS FOR THE PRODUCTION OF SPECIFIC ISOMER MIXTURES FROM OXINDOLE ALKALOIDS

[75] Inventors: Dietmar Keplinger; Klaus Keplinger; Gerhard Laus, all of Innsbruck, Austria

[73] Assignee: Immodal Pharmaka Gesellschaft m.b.H, Volders, Austria

[21] Appl. No.: 725,879

[22] Filed: Oct. 4, 1996

Related U.S. Application Data

[63] Continuation-in-part of Ser. No. 687,361, filed as PCT/AT95/00019 Jan. 31, 1995, abandoned.

[30] Foreign Application Priority Data

Feb. 4, 1994 [AT] Austria ..................... 212/94

[51] Int. Cl.$^6$ ................ C07D 209/54; C07D 209/96; C07D 471/00; C07D 491/00; C07D 498/00; C07D 513/00

[52] U.S. Cl. ................ 548/408; 548/407; 548/409; 548/410; 548/411; 546/47; 546/48; 546/49; 546/50

[58] Field of Search ................... 548/407–411; 546/47–50

[56] References Cited

PUBLICATIONS

Chemistry of Natural Compounds, vol. 12, No. 3, pp. 355–356, M.R. Sharipov et al., "Alkaloids of *Vinca erecta*" (New York 1976).

Chemistry of Natural Compounds, vol. 12, No. 2, pp. 201–202, M.R. Yagudaev et al., "Structure of Herboxine" (New York 1976).

Anales de Quimica, Ser. C, vol. 78, No. 2, pp. 180–183, J. Borges Del Castillo et al., "Flora salvadorena. V. Estudio de los alcaloides de la hamelia patens jaco" (Madrid, Spain 1982).

Phytochemistry, vol. 14, No. 2, pp. 565–568, F. Titeux et al., "Structure des caboxines: Alcaloides oxindoliques du *Cabucala fasciculata*" (France 1975).

Tetrahedron, vol. 34, No. 22, pp. 3341–3344, P.L. Majumder et al., "Stereochemistry and relative stability of the oxindoles derived from venenatine and alstovenine. The two C–3 epimeric 9–methoxy–D/E–cis–yohimbinoid alkaloids of *Alstonia venenata* R.Br." (Great Britian 1978).

J. Chromatogr., vol. 662, No. 2, pp. 243–249, G. Laus, D. Keplinger, "Separation of stereoisomeric oxindole alkaloids from *Uncaria tomentosa* by high performance liquid chromatography" (Austria 1994).

Bulletin de la Societe Chimique de France, No. 8, pp. 2766–2779, J.L. Pousset, J. Poisson, "Determination de la stereochimie des alcaloides oxindoliques" (France 1967).

Aust. J. Chem., No. 21, pp. 491–504, A.F. Beecham et al., "The Stereochemistry of Oxindole Alkaloids: Uncarines A, B (Formosanine), C (Pteropodine), D (Speciophylline), E (Isopteropodine), and F" (Austrialia 1968).

Phytochemistry, vol. 12, pp. 2795–2798, J. David Phillipson, Sarah R. Hemingway, "Oxindole Alkaloids From *Uncaria macrophylla*" (England 1973).

Lloydia, vol. 41, No. 6, pp. 503–570, J. D. Phillipson, S.R. Hemingway, "Alkaloids of Uncaria. Part V. Their Occurrence and Chemotaxonomy" (United Kingdom 1978).

*Primary Examiner*—Floyd D. Higel
*Attorney, Agent, or Firm*—Lorusso & Loud

[57] ABSTRACT

To produce defined isomer mixtures of compounds with spirocyclic beta-aminocarboxyl and/or beta-aminocarbonyl systems the invention supposes that they be dissolved in solvents which have good dissolving power for these compounds, whose relative permittivity is sufficient to stabilize the amphoteric intermediates occuring in isomerization, which as proton donors constitute hydrogen bridges, whose basicity is less than that of the compounds for isomerization and whose boiling point is so high that an adequate reaction speed can be attained by raising temperature. Further, the invention proposes that the isomerization be prevented, influenced, or terminated by altering at least one of these factors and or by altering the temperature.

33 Claims, 12 Drawing Sheets

PROCESS FOR THE PRODUCTION OF SPECIFIC ISOMER MIXTURES FROM OXINDOLE ALKALOIDS

This application is a continuation-in-part of application (s) application Ser. No. 08/687,361 filed on Aug. 2, 1996, abandoned which is the U.S. national phase of International Application PCT/AT95/00019 filed on Jan. 31, 1995, and which designated the U.S.

Compounds with a spiro β-amino carboxyl system occur naturally. They are oxindole alkaloids. Compounds with a spiro β-amino carbonyl system have not yet been found, but it is quite possible that they can be synthesized and may be used, for example, as a therapeutic agent. Under certain conditions, both of these spiro systems allow isomerization. Compounds containing such a spiro system give rise to at least two isomers. When such compounds comprise a cis ring junction they give rise to at least four isomers.

From many plants, especially of the genera Uncaria and Mitragyna, groups of two isomers, e.g. mitraphylline isomitraphylline, and groups of four isomers, e.g. pteropodine-isopteropodine-speciophylline-uncarine F, have been isolated (A. F. Phillipson, S. R. Hemingway and C. E. Ridsdale, Lloydia (J.Nat.Prod.), 41 (1978), 503). The isomerization of oxindole alkaloids has been recognized and reported on the basis of these compounds (A. F. Beecham, N. K. Hart, S. R. Johns and J. A. Lamberton, Aust.J.Chem., 21 (1968), 491; J. -L. Pousset, J. Poisson, R. J. Shine and M. Shamma, Bull.Soc.Chim.(1967), 2766). However, important conditions for the isomerization have been reported inadequately or in a misleading manner. It proved impossible to obtain definite mixtures of isomers following these literature informations. Extensive own research had to be conducted in order to make the production of defined mixtures of isomers possible in technical scale.

SOLVENTS

It is known from the literature that oxindole alkaloids undergo isomerization in polar solvents. Therefore hexafluoropropan-2-ol as a highly polar solvent was examined for its suitability as a medium for isomerization. A solution of pteropodine in hexafluoropropan-2-ol with a concentration of 18 mg/l was allowed to rest for 8 days at 20° C. Continually, samples were taken and analyzed. No isomerization was observed. Pyridine has been reported to be a suitable solvent for the isomerization, although its polarity is very low. Our results confirmed this, but only when at least small portions of water were present. This shows that the polarity of a solvent does not offer an explanation for the isomerization of oxindole alkaloids. Important causes of solvent polarity are the dielectricity constant and the ability to form hydrogen bonds. The correlation of dielectricity and rate of reaction was investigated (table 1).

TABLE 1

Correlation of the rate coefficient of isomerization of pteropodine and dielectricity constant $\epsilon$ in pure solvents at 50° C.[a]

| Solvent | $\epsilon$ (50° C.) | k |
|---|---|---|
| Formamide | 100 | 0.005 |
| Water | 70 | 1.11 |
| Dimethyl sulfoxide | ca. 46 | 0.00007 |
| Glycerol | 38 | 0.0072 |
| Methanol | 27 | 0.0020 |

TABLE 1-continued

Correlation of the rate coefficient of isomerization of pteropodine and dielectricity constant $\epsilon$ in pure solvents at 50° C.[a]

| Solvent | $\epsilon$ (50° C.) | k |
|---|---|---|
| Pyridine | 11 | 0.00002 |
| Dioxane | 2 | 0.0000004 |

[a]The rate coefficient k was determined from the initial rate of isomerization of pteropodine and, therefore, is a composite coefficient $k = k_{12} + k_{13} + k_{14}$ and has the dimension [h$^{-1}$]. The coefficient $k_{12}$ describes the transformation of pteropodine to isopteropodine, $k_{13}$ to speciophylline and $k_{14}$ to uncarine F, respectively.

It was found that the dielectricity constant cannot explain the isomerization either. But it was noticed that solvents with the ability to form hydrogen bonds, like formamide, water, glycerol or methanol, effect faster isomerization than solvents without this ability. Polar solvents are only suitable as reaction medium for the isomerization, if they possess a relatively high dielectricity constant and, as a proton donor, the ability to form hydrogen bonds. Consequently, mixtures of solvents were produced from one part with a high dielectricity constant and another part with the ability to form hydrogen bonds as a proton donor. Mixtures of one part formamide and one part alcohol turned out to be suitable reaction media.

TABLE 2

Rate of isomerization of pteropodine in mixtures of solvents at 50° C.[a]

| Solvent mixture (parts of volume) | k |
|---|---|
| Formamide-Methanol (1:1) | 0.0050 |
| Formamide-Hexafluorpropan-2-ol (1:1) | 0.0037 |
| Methanol-Dioxane (1:1) | 0.0024 |
| Methanol-Dimethyl sulfoxide (1:1) | 0.0018 |

[a]See table 1.

Water is the only solvent which combines a high dielectricity constant with the ability to form hydrogen bonds to an extent which allows satisfactory reaction rates. However, oxindole alkaloids are practically insoluble in water. Thus, it is obvious to use suitable co-solvents. It has been found that the nature of the co-solvent has an important influence on the rate of isomerization (table 3).

TABLE 3

Effect of co-solvent on the rate of isomerization of pteropodine at 50° C.[a]

| Solvent mixture | $\epsilon$ (co-solvent) | k |
|---|---|---|
| Water-Formamide (1:1) | 100 | 0.067 |
| Water-Methanol (1:1) | 27 | 0.043 |
| Water-Acetonitrile (1:1) | ca. 32 | 0.042 |
| Water-Pyridine (1:1) | 11 | 0.002 |
| Water-Dioxane (1:1) | 2 | 0.0012 |

[a]See table 1

Figure 1:
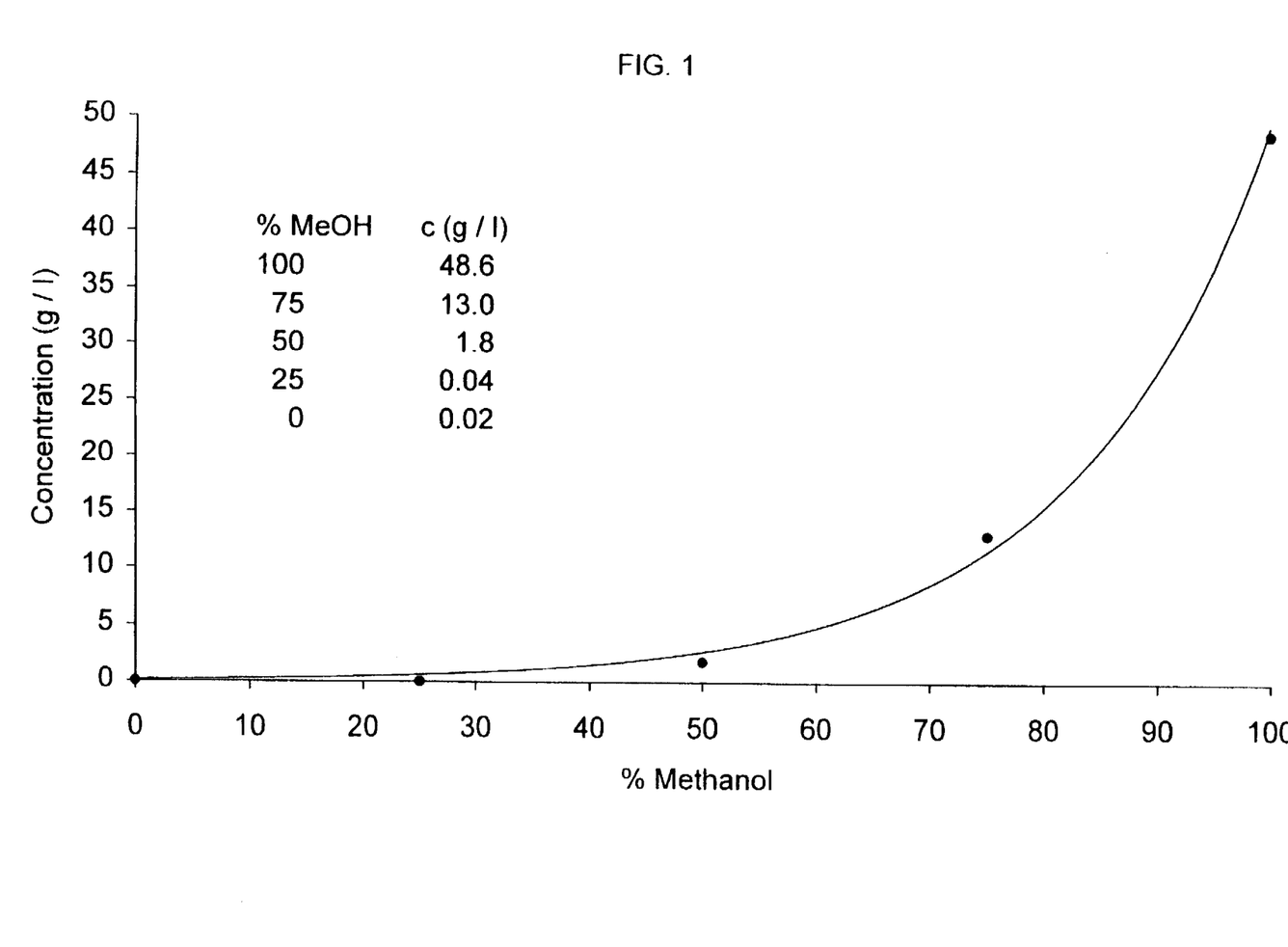
FIG. 1 is a diagram showing the solubility of pteropodine in mixtures of methanol and water at 19° C.

Only co-solvents with a dielectricity constant s higher than 20 and the ability to build up hydrogen bonds can be used for the isomerization in water. The power of solvation was found to be an exponential function of the concentration of the co-solvent in water. An example using methanol is shown in FIG. 1.

THE ISOMERIZATION

Figure 2:
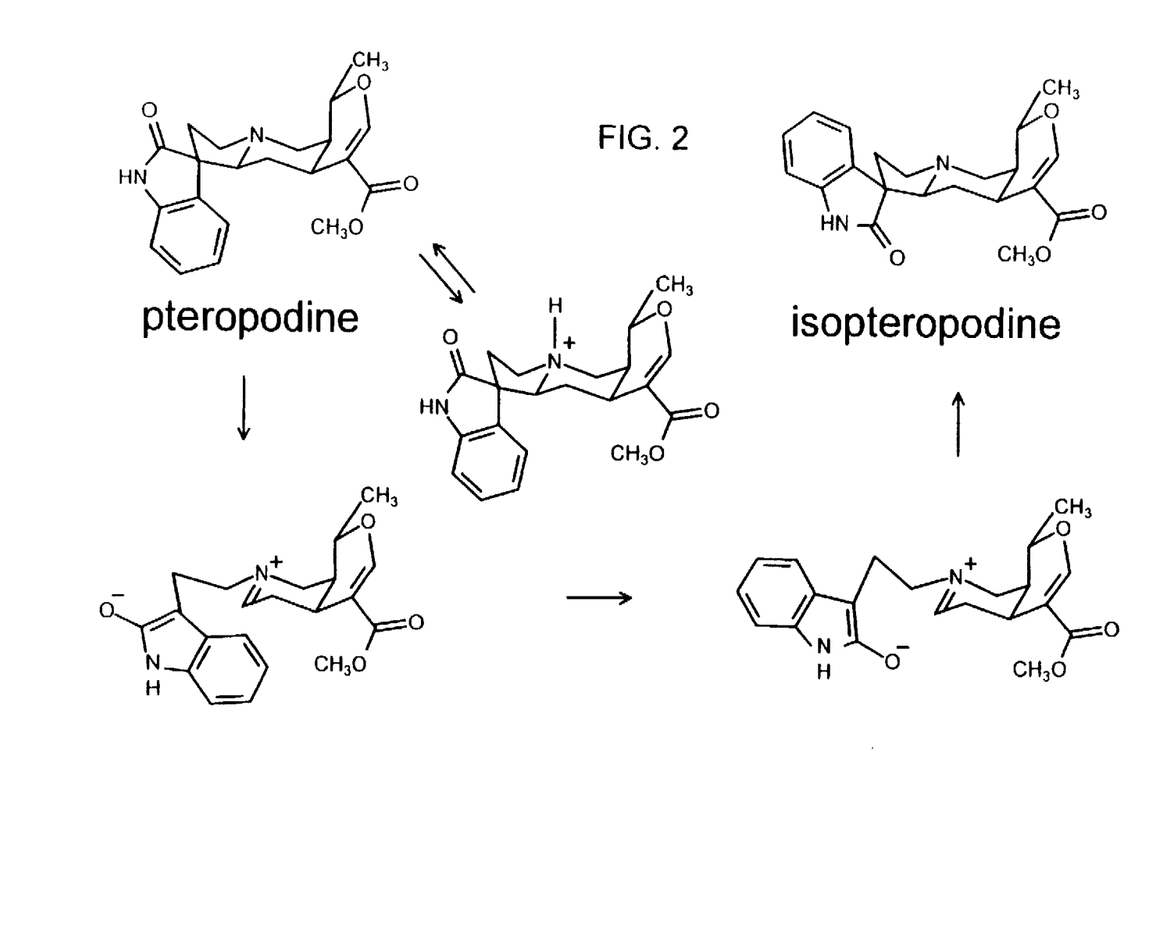
FIG. 2 shows a probable mechanism of the isomerization at the spiro centre.
Figure 3A:
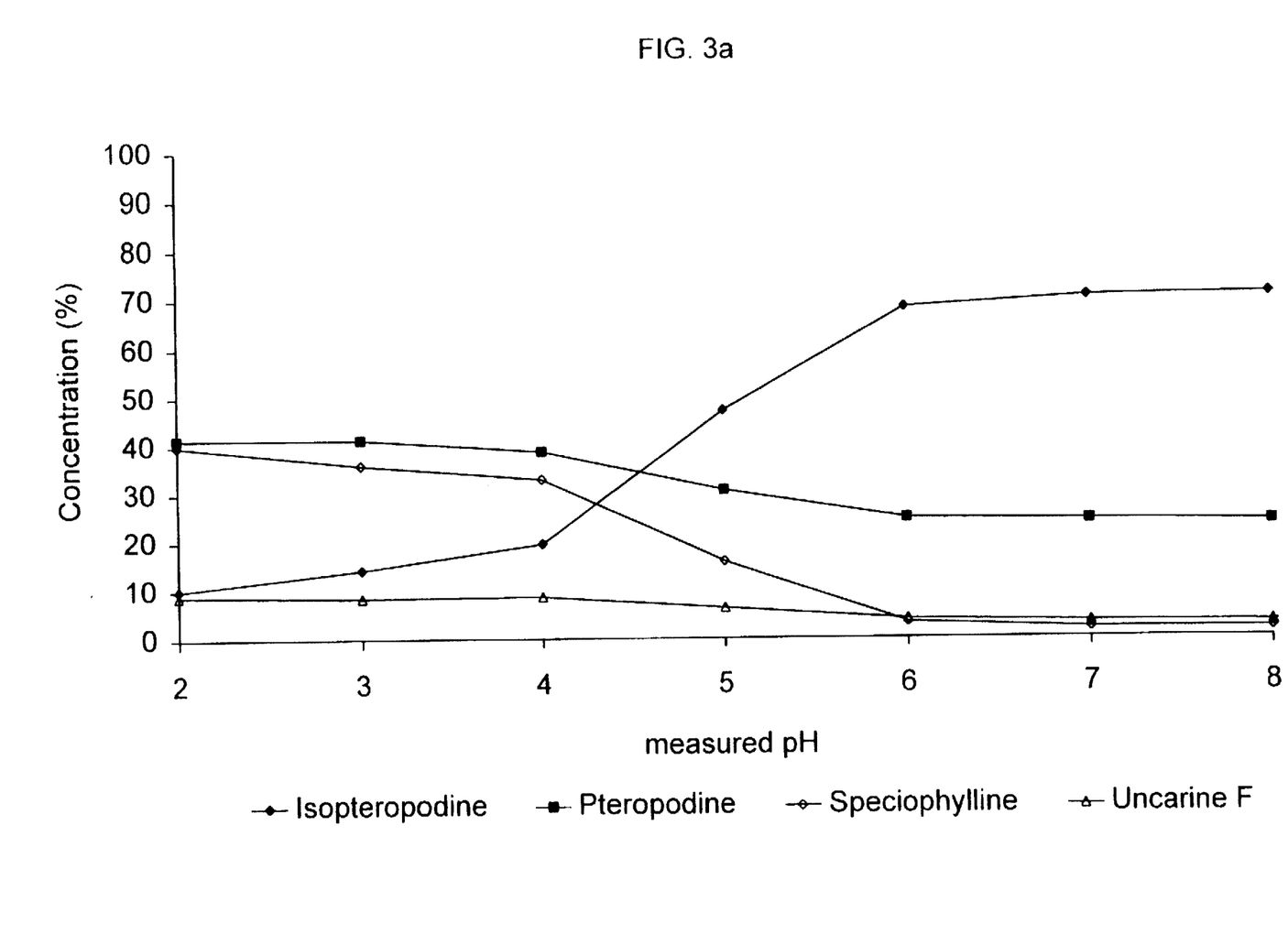
FIG. 3a is a diagram showing the dependence of the isomer distribution in equilibrium on pH as measured in methanol-water (9:1).
Figure 3B:
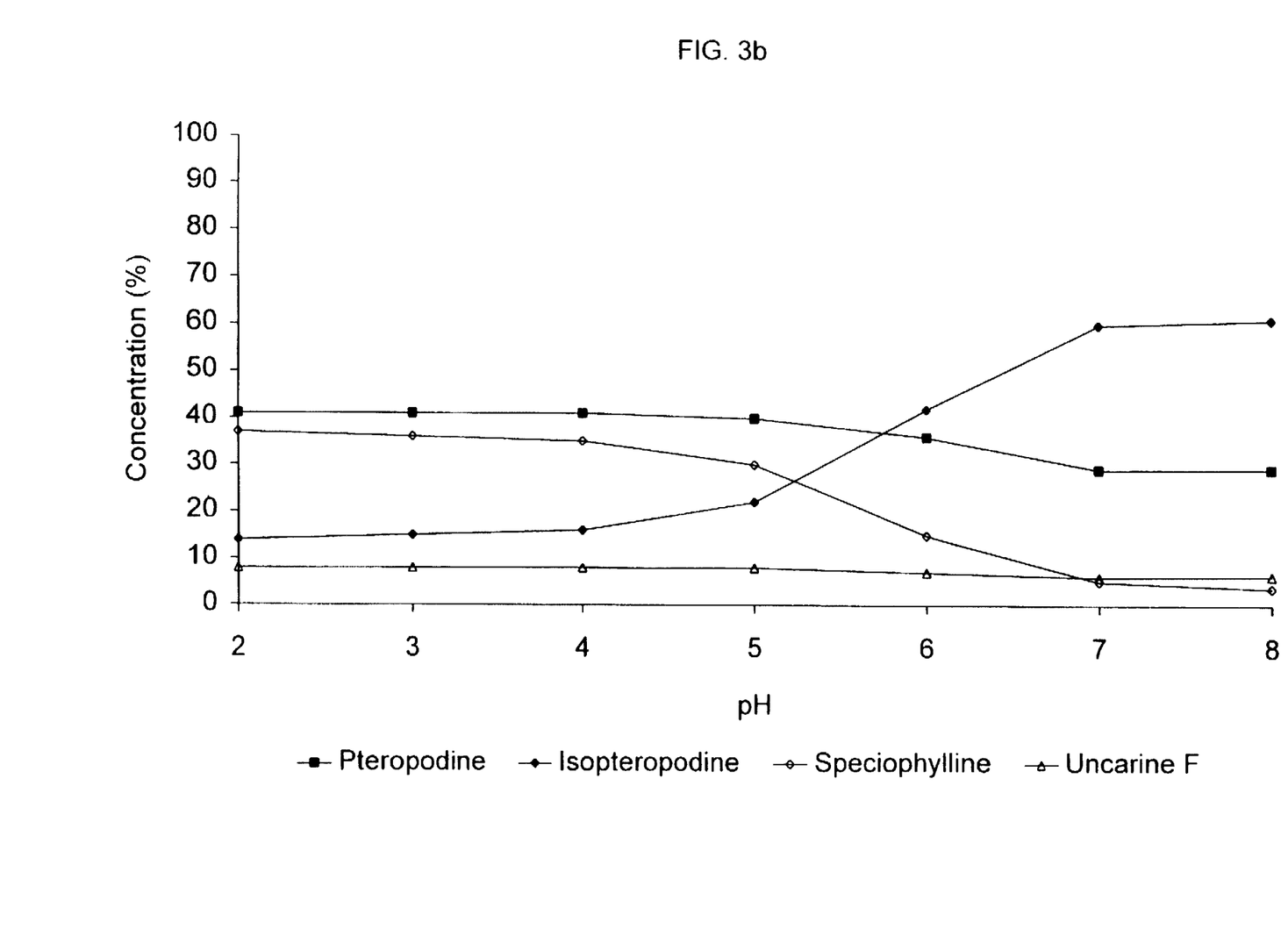
FIG. 3b is a diagram showing the dependence of the isomer distribution in equilibrium on pH in water.
Figure 4:
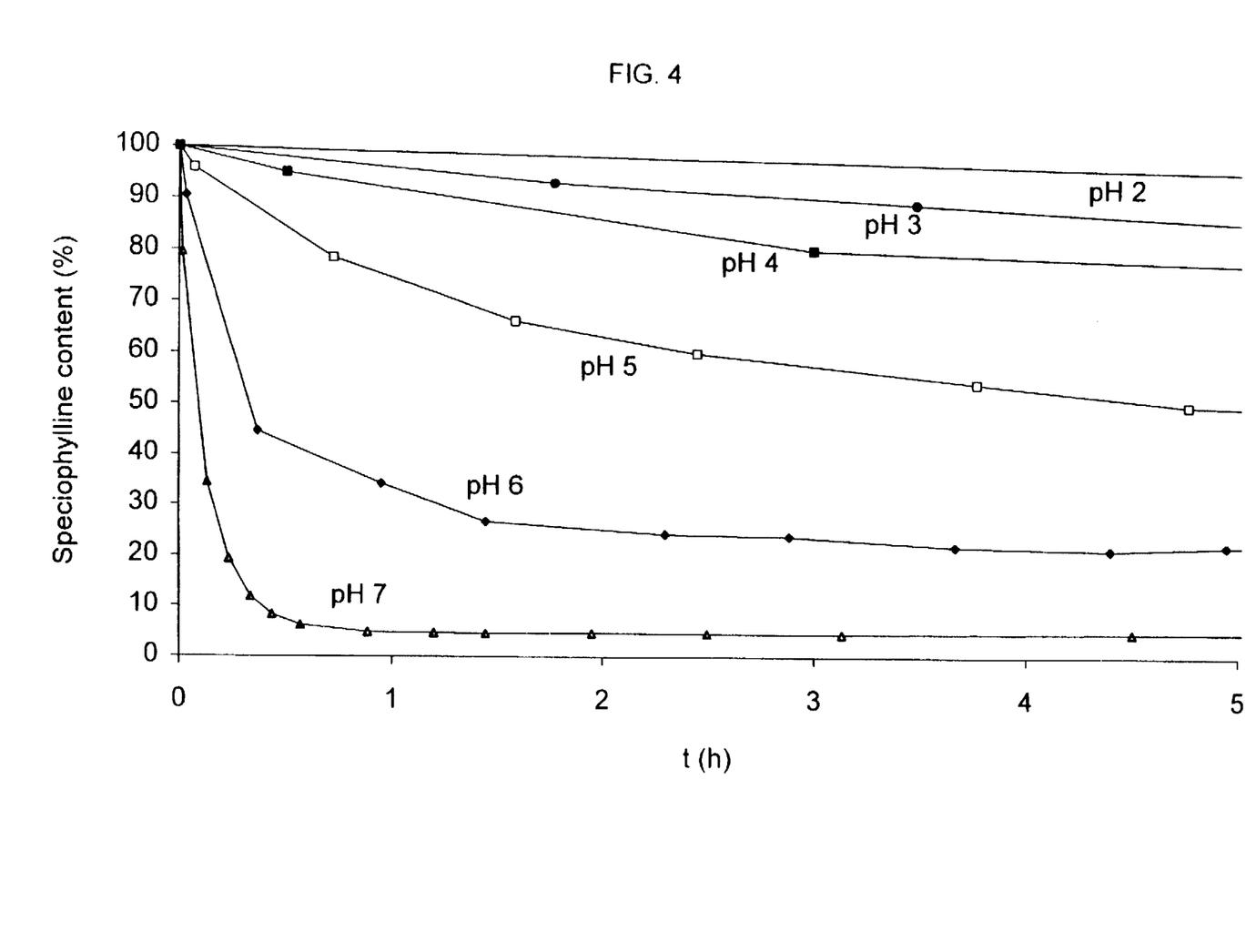
FIG. 4 is a diagram showing the effect of pH on the rate of isomerization of speciophylline in water at 50° C.
Figure 5:
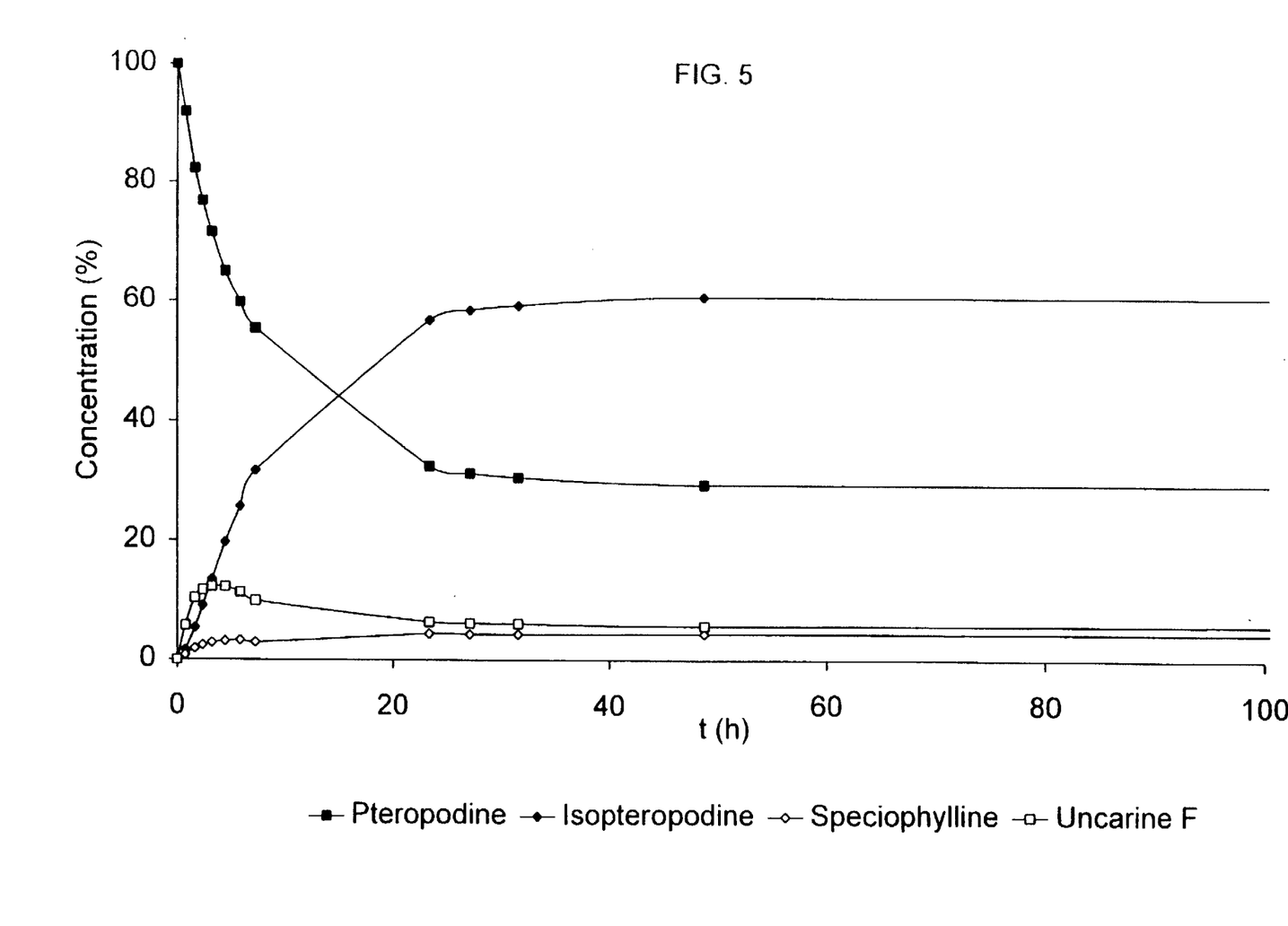
FIG. 5 is a diagram showing the course of isomerization of pteropodine in water at 37° C.
Figure 6:
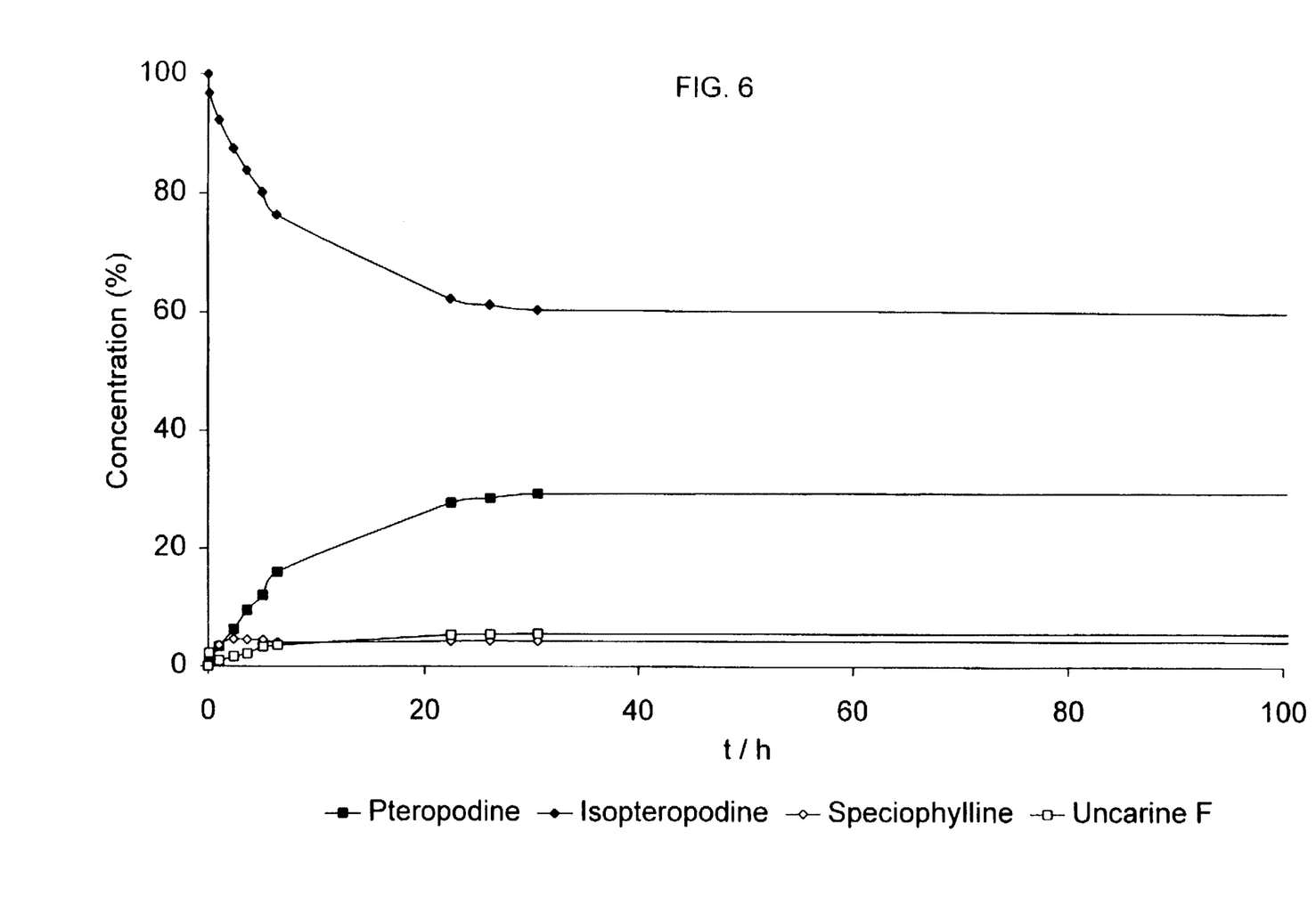
FIG. 6 is a diagram showing the course of isomerization of isopteropodine in water at 37° C.
Figure 7:
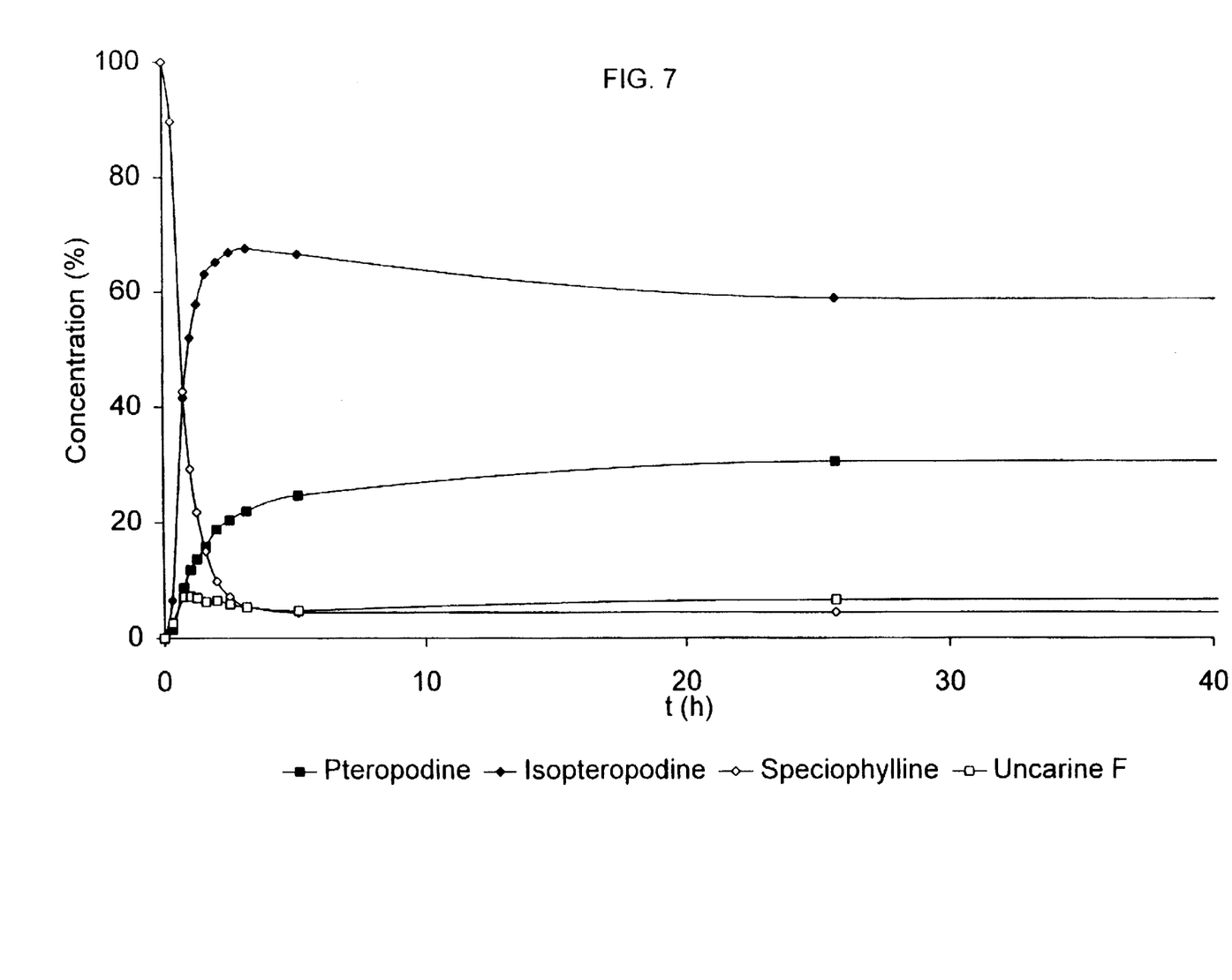
FIG. 7 is a diagram showing the course of isomerization of speciophylline in water at 37° C.
Figure 8:
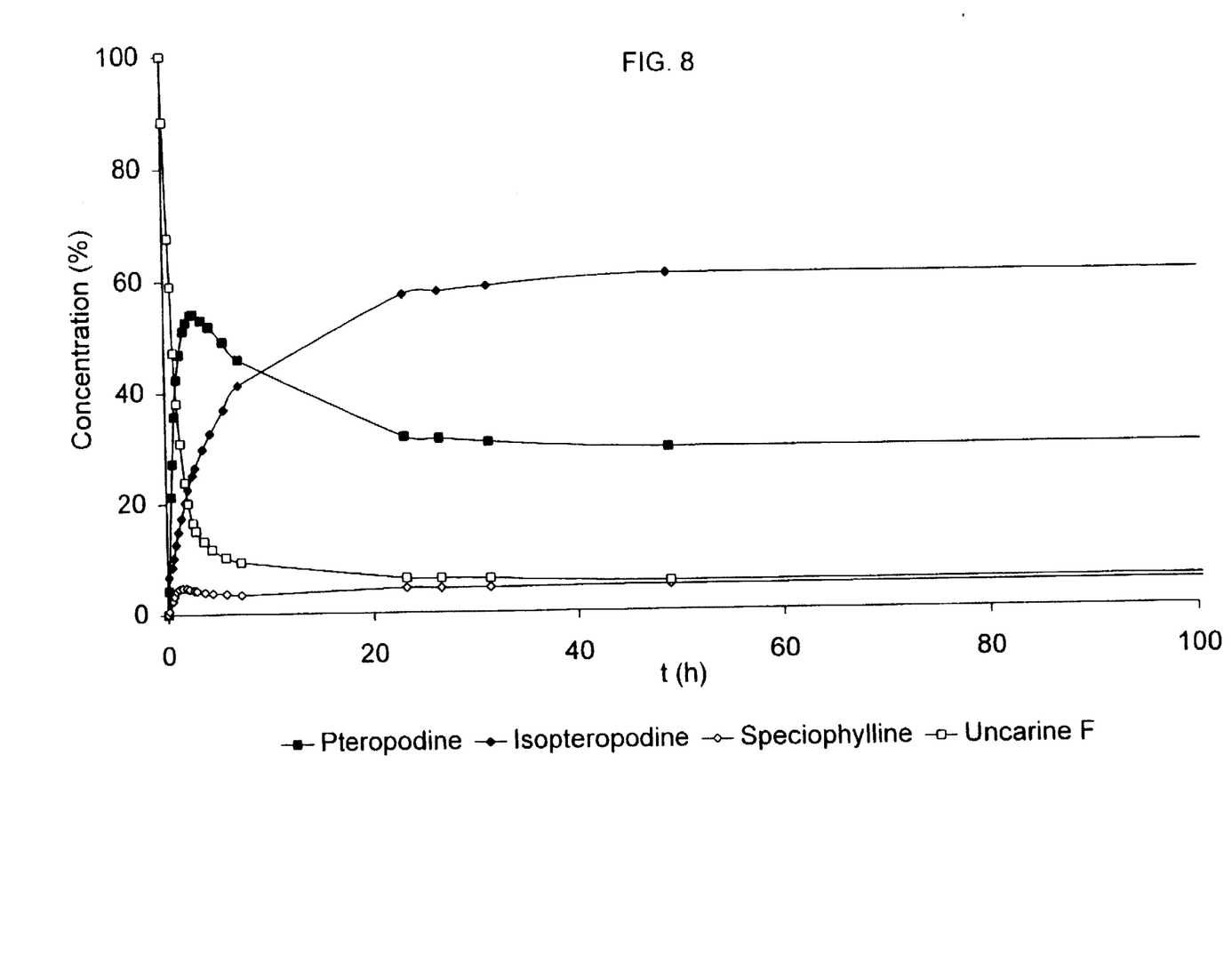
FIG. 8 is a diagram showing the course of isomerization of uncarine F in water at 37° C.

It is known from the literature (J. -L. Pousset, J. Poisson and M. Shamma, Bull.Soc.Chim. (1967), 2766) that oxindole alkaloids isomerize via a zwitterionic intermediate which is formed at the β-amino carboxyl system. There a double bond is formed between the amino nitrogen and the β-carbon, the bond between α and β-carbon is opened, and the spiro centre at the co-carbon becomes free for inversion (FIG. 2). It has also been reported that on heating with acid the isomers are preferentially formed which exhibit the proton at the amino nitrogen and the carboxyl oxygen in a syn position, while on heating in pyridine the isomers with anti configuration are preferred (J. D. Phillipson and S. R. Hemingway, Phytochemistry (1973), 12, 2795). Our investigations showed that different values of pH gave different equilibria of isomers. The pH of a mixture of 9 parts of water and 1 part of methanol was adjusted to values from 2 to 9 by addition of phosphoric acid or sodium hydroxide, respectively. Pteropodine (c=30 mg/l) was isomerized in these solvents until the equilibrium was reached. The mixtures obtained in acidic solutions depended characteristically on the pH value, but were independent of pH in neutral or alkaline solutions (FIG. 3a). The dependence of the pteropodine equilibrium on pH in pure water was investigated, too (FIG. 3b). It was also noticed that the rate of reaction decreased with increasing proton concentration. (FIG. 4).

TABLE 4

Effect of temperature and solvent on the equilibrium composition of the pteropodine isomers (temperature from 25 to 50° C., % per weight)

| T (°C.) | Alkaloid | Solvent | |
|---|---|---|---|
| | | Water | Methanol |
| 25 | Pteropodine | 29.6% | 22.9% |
| | Isopteropodine | 60.9% | 75.4% |
| | Speciophylline | 4.3% | 0.4% |
| | Uncarine F | 5.2% | 1.3% |
| 37 | Pteropodine | 29.8% | 22.6% |
| | Isopteropodine | 59.6% | 75.5% |
| | Speciophylline | 4.5% | 0.5% |
| | Uncarine F | 6.1% | 1.4% |
| 50 | Pteropodine | 29.6% | 23.5% |
| | Isopteropodine | 59.4% | 73.5% |
| | Speciophylline | 4.6% | 1.0% |
| | Uncarine F | 6.4% | 2.0% |

The use of solvents with different polarity gave different equilibria, while other conditions were identical. Temperature also had a small influence on the equilibria (tables 4 and 5).

TABLE 5

Effect of temperature and solvent on the equilibrium composition of the mitraphylline isomers (temperature from 25 to 50° C., % per weight)

| T (°C.) | Alkaloid | Solvent | |
|---|---|---|---|
| | | Water | Methanol |
| 25 | Mitraphylline | 34.4% | 22.5% |
| | Isomitraphylline | 65.6% | 77.5% |
| 37 | Mitraphylline | 32.5% | 25.0% |
| | Isomitraphylline | 67.5% | 75.0% |
| 50 | Mitraphylline | 32.0% | 26.3% |
| | Isomitraphylline | 68.0% | 73.7% |

The four isomeric oxindole alkaloids pteropodine, isopteropodine, speciophylline and uncarine F were dissolved in water (c=18 mg/l) and isomerized at 37° C. for 100 hours. Continually, samples were taken and the composition was analyzed (FIGS. 5, 6, 7 and 8).

Figure 9:
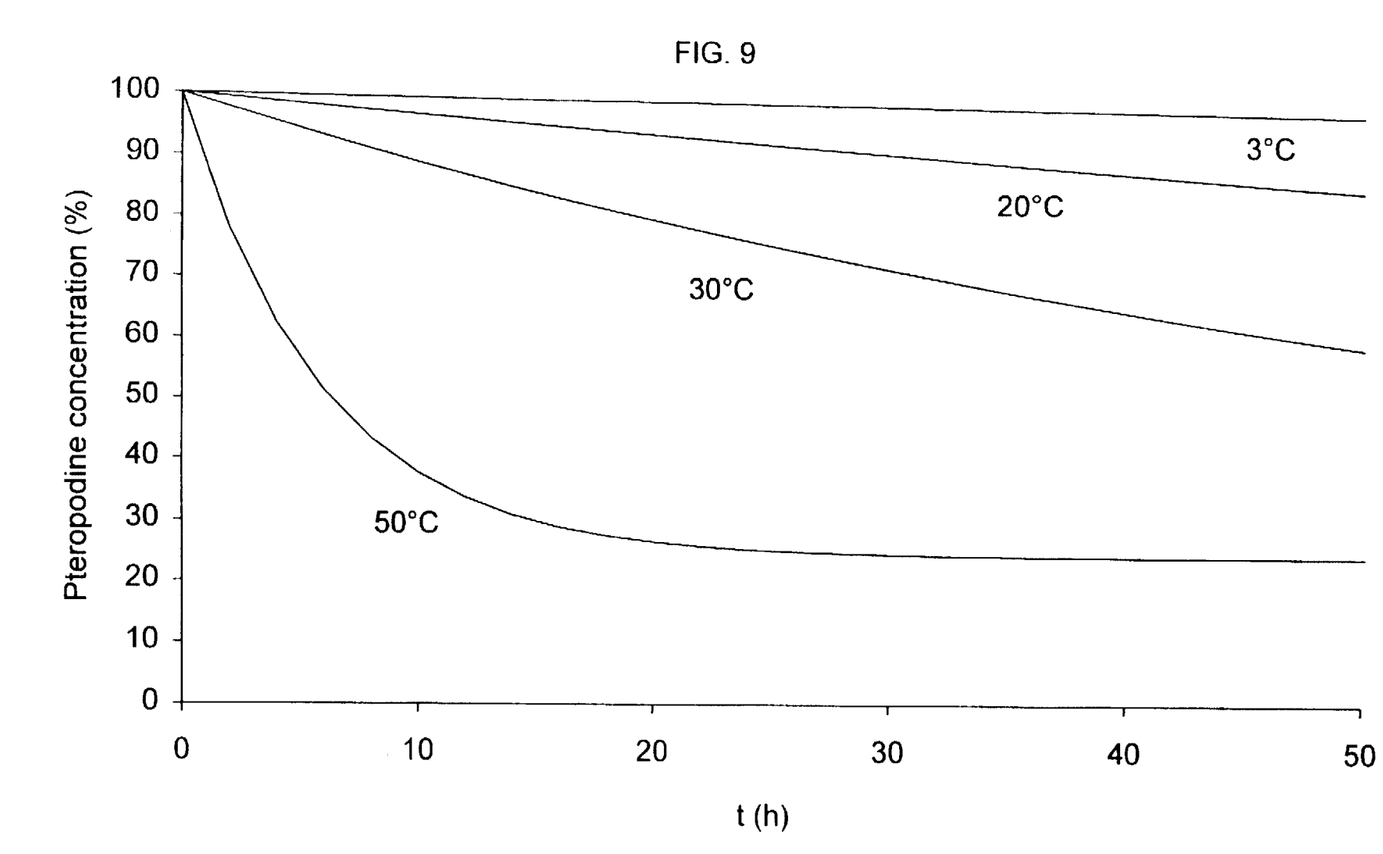
FIG. 9 is a diagram showing the effect of temperature on the rate of isomerization of pteropodine in a mixture of water and methanol (7:3).

It was found that under identical conditions the various isomers isomerized at different rates. The effect of temperature on the rate of reaction was investigated. Pteropodine was dissolved in water (c=20 mg/l) and isomerized at various temperatures for 50 hours. The reactions were monitored (FIG. 9). An increase of temperature by 12° C. accelerated the reaction by a factor of 5.

DISTRIBUTION EFFECTS

Figure 11:
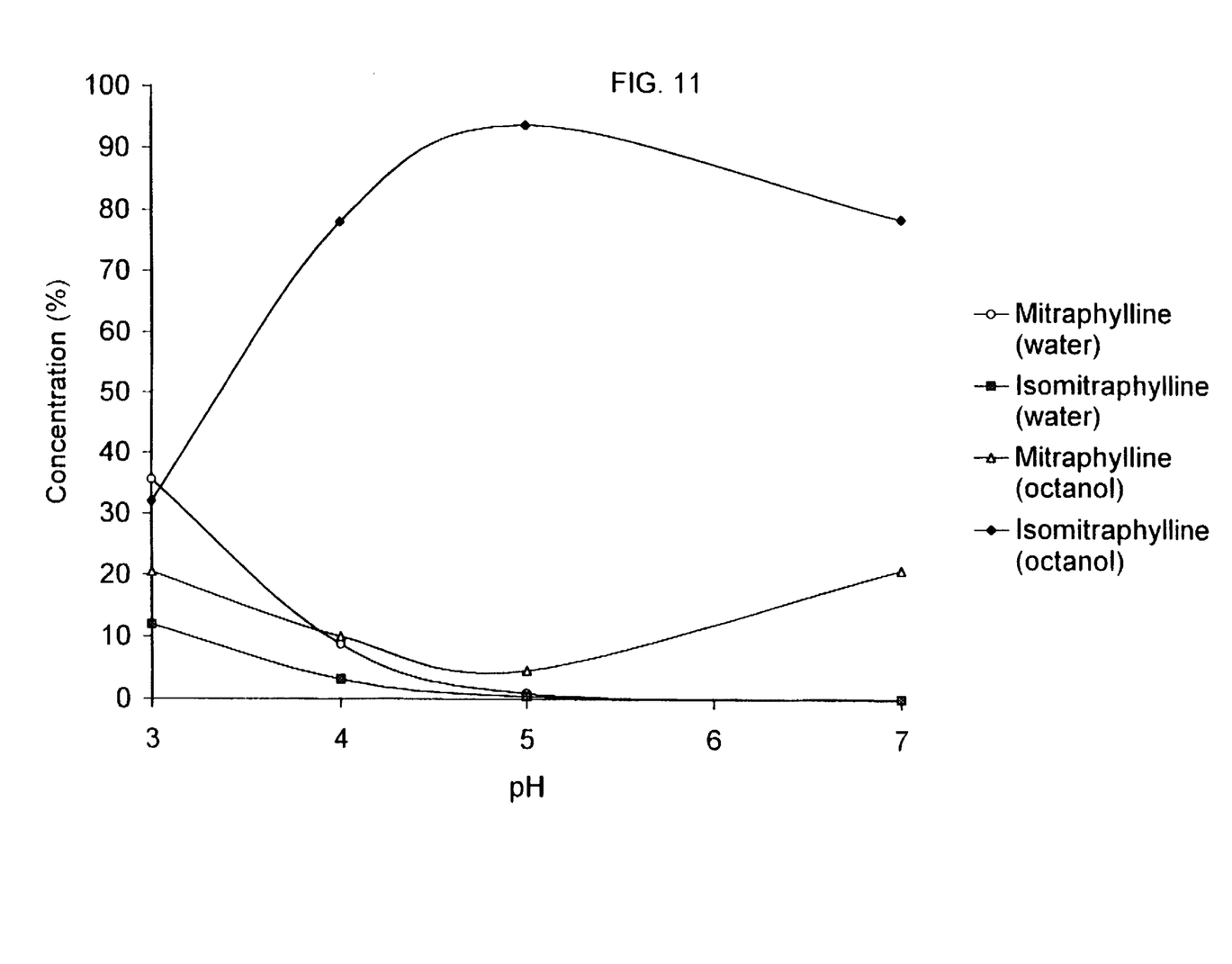
FIG. 11 is a diagram showing the dependence of the isomer distribution in equilibrium on pH in octanol/water.

It was found that each isomer had a different coefficient of distribution between water and an immiscible organic solvent. Protonation of the alkaloid hinders partition into the solvent, but the dependence of the distribution coefficient on pH is different for each isomer due to their different basicity. When the isomerization takes place in such a two-phase system, the equilibrium obtained in the organic phase is different from that in the aqueous phase. As an example, the coefficients of distribution $K_{o/w}$ of mitraphylline and isomitraphylline between 1-octanol and water at three pH values and the corresponding equilibria are given in table 6 (FIG. 11).

TABLE 6

Coefficients of distribution between 1-octanol and water $K_{O/W}$ for mitraphylline and isomitraphylline and the resulting equilibria as a function of pH at 25° C. (% per weight).

| pH | 3 | 5 | 7 |
|---|---|---|---|
| log $K_{O/W}$ (Mitraphylline) | −0.24 | 0.67 | 2.5 |
| log $K_{O/W}$ (Isomitraphylline) | 0.43 | 2.3 | 2.8 |
| Mitraphylline (water) | 35.6% | 1.0% | 0.12% |
| Isomitraphylline (water) | 11.9% | 0.5% | 0.08% |
| Mitraphylline (octanol) | 20.5% | 4.6% | 21.0% |
| Isomitraphylline (octanol) | 32.0% | 93.9% | 78.8% |

The production of defined mixtures of compounds with a spiro β-amino carboxyl and/or β-amino carbonyl system is not possible in technical scale under the conditions described in the literature. Neither solubility nor time of reaction have been taken in account in the literature. Conditions of the reaction have not been specified in a detailed manner.

It is therefore an object of the invention to provide a method for preparing a mixture of isomers of a spirocyclic oxindol alkaloid, in which mixture the isomeric pattern can be selected.

It is another object of the invention to provide a method for preparing a mixture of isomers of a spirocyclic oxindol alkaloid without changing the equilibrium of isomers given originally, e.g. as it occurs in a plant.

It is another object of the invention to provide a method for preparing an isomer of a spirocyclic oxindol alkaloid from a mixture of isomers.

SUMMARY OF THE INVENTION

Our investigations have shown that only certain solutions allow a technically useful isomerization. Such solutions must comprise:
1. They must have a relatively high dielectricity constant.
2. They must be proton donors able to form hydrogen bonds.
3. They must have good solvating properties for the compounds to be isomerized.

Preferably none of their components should have a basicity higher than the compounds to be isomerized, and, furthermore, none of its components should depress the boiling point of the mixture so far that suitable energy supply for the isomerization becomes impossible.

Figure 10:
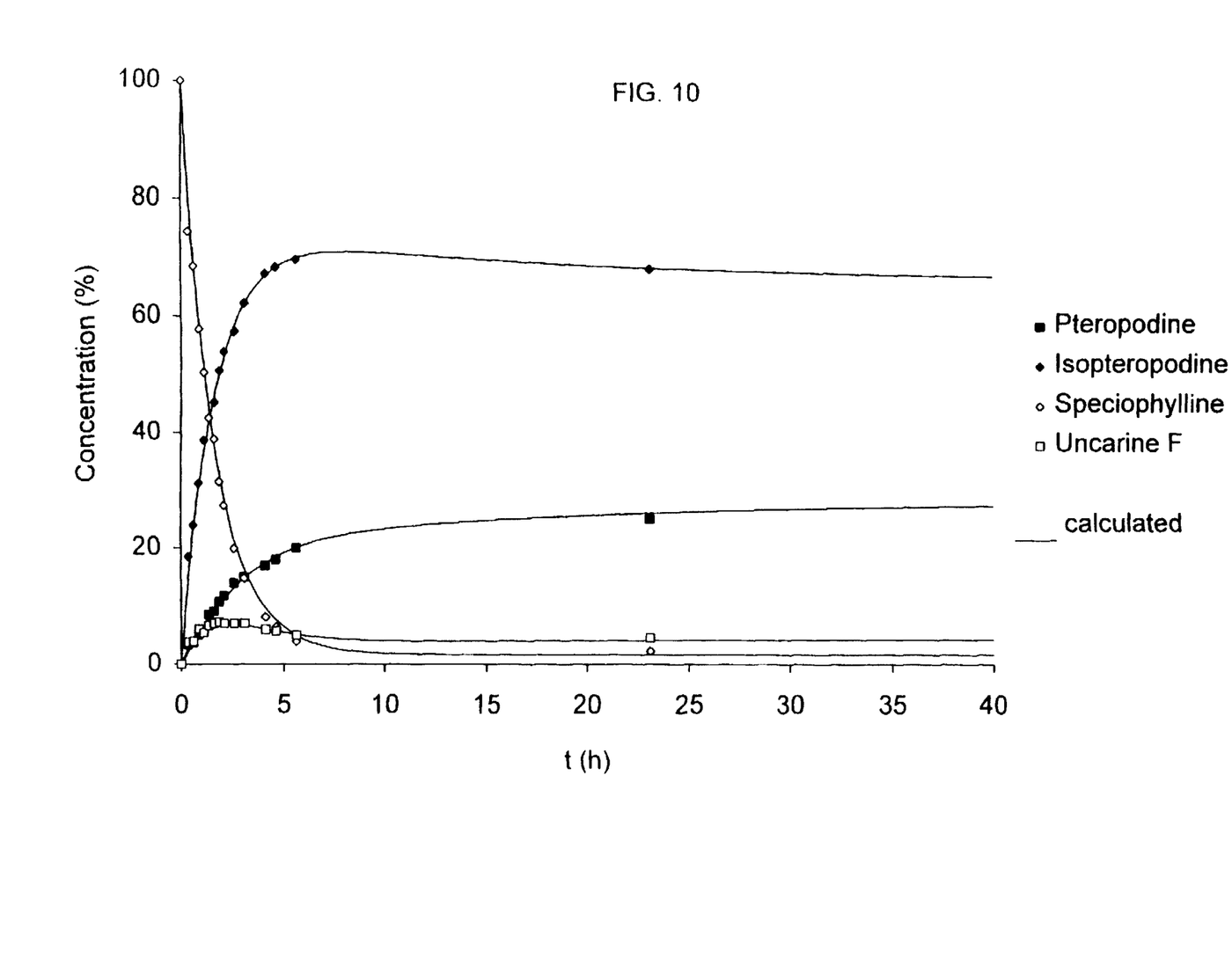
FIG. 10 is a diagram showing the comparison of measured and calculated course of isomerization of speciophylline in water at 37° C.

Pure solvents possessing these properties are not known. This invention proposes mixtures of solvents which, on the basis of their initial composition, in-process change of composition or of temperature, allow the production of specific mixtures of isomers. A calculation program was developed in order to allow a specific application of this process. Thus, for particular solvents at particular temperatures the course of isomerization can be calculated and the time to stop the reaction can be determined (FIG. 10).

On the other hand, the invention proposes solvents which have a relatively low dielectricity constant, when it is desirable to maintain a specific mixture of isomers without any change in composition, e.g. as it occurs naturally in a plant.

BRIEF DESCRIPTION OF THE DRAWINGS

Further advantages of the invention will be explained below in greater detail with reference to the accompanying drawings in which.

PREFERRED EXAMPLES

A typical example of this invention is the production of pteropodine from any mixture of isomers of this group. The initial mixture is refluxed in water at pH 2 for 48 hours, then cooled to at least room temperature and neutralized. The alkaloids precipitate and are extracted with diethyl ether. This solution is dried over anhydrous magnesium sulfate and the solvent evaporated. The product mixture from this first step is dissolved in methanol-water (2:8) and isomerized for 3 hours at 37° C. Then, the reaction is stopped by cooling. The alkaloids are extracted with diethyl ether again. After drying with magnesium sulfate the solvent is evaporated. The composition of the mixture at this time is 46% per weight pteropodine, 37% per weight isopteropodine, 11% per weight speciophylline and 6% per weight uncarine F. The mixture then is dissolved in boiling t-butyl methyl ether and slowly cooled to 18° C. Pteropodine crystallizes and can be removed by filtration in a high degree of purity. The alkaloids remaining in the mother liquor can be obtained by evaporation of the solvent and can be fed into the same process again.

Another typical example is the production of isopteropodine. Any mixture of the pteropodine isomers is dissolved in a mixture of one part water and one part methanol (1:1) at pH 7 and the solution is kept at 50° C. for 60 hours. Acetic acid is added to a final concentration of 0.2 mol/l. The bulk of methanol is distilled off under reduced pressure. The concentrated solution is cooled and isopteropodine precipitates.

Another method for the production of isopteropodine starts from speciophylline which is dissolved in methanol and kept at 50° C. for 50 hours. An accumulation of 70% per weight isopteropodine is obtained. The methanol is distilled off and acetic acid (0.2 mol/l) is added to the residue. Pure isopteropodine can be collected by filtration.

The two other isomers of the pteropodine group can be produced by refluxing any mixture of the isomers in water at pH 2 for 48 hours. Then, the solution is cooled and neutralized. The alkaloids are extracted with diethyl ether, the solution is dried over magnesium sulfate and the solvent evaporated. Speciophylline is separated by column chromatography using silica gel and ethyl acetate-methanol (9:1) as the eluent. In order to obtain uncarine F the product mixture from the first step is dissolved in t-butyl methyl ether and cooled slowly. Pteropodine and speciophylline are precipitated and removed by filtration. They can be fed into the same process again. The filtrate is enriched in uncarine F, which is purified by column chromatography.

The two mitraphylline isomers are produced by dissolving any mixture of them in water at pH 2 for mitraphylline, or in methanol-water for isomitraphylline, respectively. The solution is kept at 50° C. for 10 hours and then cooled. In the case of mitraphylline production, the methanol is distilled off. The alkaloids are extracted with diethyl ether. On concentrating the solution mitraphylline crystallizes and is collected by filtration. The filtrate is brought to dryness and yields isomitraphylline.

The two rhynchophylline isomers are produced in the same manner as the mitraphyllines. For purification, column chromatography on silica gel with ethyl acetate-methanol (9:1) is preferred.

The alkaloid pattern in freshly harvested plant material of *Uncaria tomentosa* is specifically altered by gassing the cut material with hydrogen chloride. The mixture is maintained at 30°–40° C. for seven days in a tight vessel and then dried. Now pteropodine, speciophylline and mitraphylline are the main components.

Another method of selectively changing the alkaloid pattern of plant material is soaking it with dilute ammonia and maintaining it at 50° C. for six hours. The composition of the alkaloids as shown in FIG. 3b above pH 7 is obtained after drying.

The knowledge of this invention can be used to check whether isomerization has taken o place during production of plant extracts or preparations thereof, because the natural oxindole alkaloid distribution in plants never matches an equilibrium mixture. When the share of speciophylline in the total pteropodine isomers is smaller than 20% and/or that of uncarine F is smaller than 10%, isomerization must have taken place. In general, whenever the isomer ratio of a mixture approaches a pH dependent equilibrium, it is evident that isomerization has been performed. A specific isomer mixture has also been produced in the sense of this invention when the naturally occuring alkaloid pattern has been retained by protonation of the amino nitrogen atom during extraction. In this case, an acid or a salt thereof will be detected in unnaturally high concentration in the extract.

We claim:

1. A method of preparing a mixture of isomers of a spiro oxindole alkaloid, said mixture having a definable isomer pattern, said method comprising:

defining said isomer pattern of said mixture of isomers, selecting an organic solvent being able to dissolve said oxindole alkaloid and being homogeneously miscible with water, selecting a concentration of said organic solvent, said concentration determining said defined isomer pattern, preparing a homogeneous solvent-agent comprising water and said organic solvent, and dissolving said oxindole alkaloid in said solvent-agent, said oxindole alkaloid being isomerized into said mixture of isomers according to said isomer pattern.

2. A method according to claim 1, wherein said solvent-agent has a dielectric constant $\epsilon$ higher than 20.

3. A method according to claim 1, wherein said organic solvent agent is a proton donor able to form hydrogen bonds.

4. A method according to claim 1, further comprising controlling the rate of isomerisation by selecting the pH-value of said solvent-agent.

5. A method according to claim 1, further comprising controlling the rate of isomerisation by selecting the temperature of said solvent-agent.

6. A method according to claim 1, wherein isomerisation is terminated at said defined isomer pattern.

7. A method according to claim 6, wherein isomerisation is terminated by quaternization of the amino nitrogen of said oxindole alkaloid.

8. A method according to claim 7, wherein isomerisation is terminated by protonation of the amino nitrogen of said oxindole alkaloid.

9. A method according to claim 1, wherein said oxindole alkaloid is contained in plant material to be extracted.

10. A method according to claim 1 further comprising removing said solvent-agent from said mixture of isomers, and stabilizing said mixture of isomers in a non-aqueous solvent.

11. A method of preparing a mixture of isomers of a spiro oxindole alkaloid, said mixture having a definable isomer pattern, said method comprising:

defining said isomer pattern of said mixture of isomers, selecting an organic solvent being able to dissolve said oxindole alkaloid and being heterogeneously miscible with water, preparing a heterogeneous solvent mixture comprising water and said organic solvent, and dissolving said oxindole alkaloid in said heterogeneous solvent mixture, said oxindole alkaloid being isomerized into said mixture of isomers according to said isomer pattern.

12. A method according to claim 11, wherein said solvent mixture further comprises a second organic solvent being able to dissolve said oxindole alkaloid and being homogeneously miscible with water.

13. A method according to claim 12, wherein said second organic solvent has a dielectric constant of $\alpha$ higher than 20.

14. A method according to claim 12, wherein said second organic is a proton donor able to form hydrogen bonds.

15. A method according to claim 12 further comprising controlling the rate of isomerisation by selecting the pH-value of said water of said solvent mixture.

16. A method according to claim 11 further comprising controlling the rate of isomerisation by selecting the temperature of said solvent mixture.

17. A method according to claim 11, wherein isomerisation is terminated at said defined isomer pattern.

18. A method according to claim 17, wherein isomerisation is terminated by quaternization of the amino nitrogen of said oxindole alkaloid.

19. A method according to claim 17, wherein isomerisation is terminated by protonation of the amino nitrogen of said oxindole alkaloid.

20. A method according to claim 11, wherein said oxindole alkaloid is contained in plant material to be extracted.

21. A method according to claim 11 further comprising removing said solvent mixture from said mixture of isomers, and stabilizing said mixture of isomers in a non-aqueous solvent.

22. A method of preparing a defined mixture of isomers of a spiro oxindole alkaloid having an initial pattern of isomers, said method comprising:

selecting an organic solvent being able to dissolve said oxindole alkaloid without changing said pattern and having a dielectric constant $\epsilon$ lower than 20 and dissolving said oxindole alkaloid in said organic solvent, said oxindole alkaloid being isomerized into said mixture of isomers according to initial pattern of isomers.

23. A method according to claim 22, wherein said oxindole alkaloid is contained in plant material to be extracted.

24. A method according to claim 22 further comprising removing said organic solvent from said mixture of isomers, and dissolving said mixture of isomers in a homogeneous solvent-agent comprising water and an organic solvent.

25. A method according to claim 22, wherein said mixture of isomers is stabilized in a non-aqueous solvent.

26. A method of preparing a defined mixture of isomers of a spiro oxindole alkaloid having an initial pattern of isomers, said method comprising:

selecting an organic solvent being able to dissolve said oxindole alkaloid without changing said pattern and being unable to form hydrogen bonds and dissolving said oxindole alkaloid in said organic solvent, said oxindole alkaloid being isomerized into said mixture of isomers according to initial pattern of isomers.

27. A method according to claim 26, wherein said oxindole alkaloid is contained in plant material to be extracted.

28. A method according to claim 26 further comprising removing said organic solvent from said mixture of isomers, and dissolving said mixture of isomers in a homogeneous solvent-agent comprising water and organic solvent.

29. A method according to claim 26, wherein said mixture of isomers is stabilized in a non-aqueous solvent.

30. A method of preparing an isomer of a spiro oxindole alkaloid, said method comprising:

selecting a first solvent being able to dissolve said oxindole alkaloid and being miscible with water, preparing a solvent mixture containing water and said first solvent, dissolving said oxindole alkaloid in said solvent mixture, said oxindole alkaloid being isomerized into said mixture of isomers, removing said solvent mixture from said mixture of isomers, selecting a second solvent having different solvating abilities for each isomer of said mixture of isomers, selecting the solvating ability of said second solvent corresponding to said isomer of said oxindole alkaloid.

re-dissolving said mixture of isomers in said second solvent, and altering said second solvent to precipitate said isomer of said oxindole alkaloid.

31. A method according to claim 30, wherein said oxindole alkaloid is precipitated by cooling said second solvent.

32. A method according to claim 30, wherein said oxindole alkaloid is contained in plant material to be extracted.

33. A method according to claim 30, wherein said isomer is fixed in a non-aqueous-solvent.

* * * * *